(12) United States Patent
Chen et al.

(10) Patent No.: US 8,110,580 B2
(45) Date of Patent: *Feb. 7, 2012

(54) THIOPHENE PYRAZOLOPYRIMIDINE COMPOUNDS

(75) Inventors: Zhaogen Chen, Indianapolis, IN (US); Shaojuan Jia, Zionsville, IN (US); James Lee Toth, Knightstown, IN (US)

(73) Assignee: Eli Lilly and Company, Indianapolis, IN (US)

( * ) Notice: Subject to any disclaimer, the term of this patent is extended or adjusted under 35 U.S.C. 154(b) by 77 days.

This patent is subject to a terminal disclaimer.

(21) Appl. No.: 12/438,953

(22) PCT Filed: Sep. 13, 2007

(86) PCT No.: PCT/US2007/078352
§ 371 (c)(1),
(2), (4) Date: Feb. 26, 2009

(87) PCT Pub. No.: WO2008/036541
PCT Pub. Date: Mar. 27, 2008

(65) Prior Publication Data
US 2010/0022560 A1      Jan. 28, 2010

Related U.S. Application Data

(60) Provisional application No. 60/826,273, filed on Sep. 20, 2006.

(51) Int. Cl.
A61K 31/519     (2006.01)
A01N 43/90      (2006.01)
C07D 487/00     (2006.01)

(52) U.S. Cl. .................. 514/259.31; 544/281
(58) Field of Classification Search .......... None
See application file for complete search history.

(56) References Cited

U.S. PATENT DOCUMENTS 7,612,067 B2 * 11/2009 Barbosa et al. ............ 514/233.2

FOREIGN PATENT DOCUMENTS

| WO | WO 94/13676 | 6/1994 |
| WO | WO 97/29109 | 8/1997 |
| WO | WO 98/03510 | 1/1998 |
| WO | WO 98/08847 | 3/1998 |
| WO | WO 01/23388 | 4/2001 |
| WO | WO 2005/063755 | 7/2005 |
| WO | WO 2006/102194 | * 9/2006 |

OTHER PUBLICATIONS

Williams et al (Foye's Principles of Medicinal Chemistry, 5th Edition, Pages , 2002).*
Patani et al (Chem Rev 96:3147-3176, 1996).*
Majo,. V.J. et al., <<Palladium-Catalyzed Synthesis of 3-Arylpyrazolo-[1,5a]pyrimidines >> Advanced Synthesis and Catalysis, Wiley, Weinheim, DE, vol. 345(5) 620-624—XP002468036, (May 5, 2003).
Chen, et al., Design of 2,5-Dimethyl-3-(6-dimethyl-4-methylpyridin-3-yl)-7-dipropyl aminopryazolo[1,5-a]pyrimidine (NBI 30775/R121919) and Structure-Activity Relationships of a Series of Potent and Orally Active Corticotropin-Releasing Factor Receptor Antagonists', J. O Medicinal Chemistry Society. Washington, US.47(19) 4787-4798, XP001206057 (2004).
Gilligan, P., et al., <<The Discovery of 4-(3-Pentylamino)-2,7-dimethyl-8-(2-methyl-4-methoxyphenyl)-pyrazolo-[1,5-α]-pyrimidine: A corticotrophin-Releasing Factor (hCRF1)Antagonist; *Bioorganic & Medicinal Chemistry* 8, 181-189 (2000).

* cited by examiner

*Primary Examiner* — Brandon Fetterolf
*Assistant Examiner* — Craig Ricci
(74) *Attorney, Agent, or Firm* — R. Craig Tucker

(57) ABSTRACT

The present invention relates to compounds of Formula (I), pharmaceutical compositions thereof, and the use of such compounds as corticotropin releasing factor 1 (CRF1) receptor antagonists in the treatment of psychiatric and neuroendocrine disorders, neurological diseases, and metabolic syndrome.

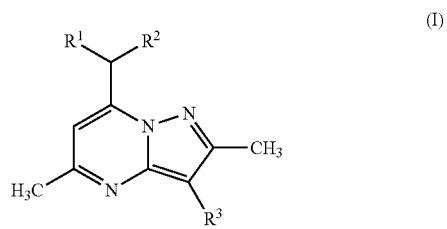

4 Claims, No Drawings

THIOPHENE PYRAZOLOPYRIMIDINE COMPOUNDS

This U.S. national stage application of International Application PCT/US2007/078352, filed Nov. 13, 2007, claims priority to U.S. provisional application Ser. No. 60/826,273, filed Sep. 20, 2006.

FIELD OF THE INVENTION

This invention relates to novel thiophene pyrazolopyrimidine compounds, pharmaceutical compositions thereof, and use thereof as CRF1 receptor antagonists in the treatment of psychiatric and neuroendocrine disorders, neurological diseases, and metabolic syndrome.

BACKGROUND OF THE INVENTION

Corticotropin releasing factor (CRF) is a 41 amino acid peptide that is the primary physiological regulator of proopiomelanocortin (POMC) derived peptide secretion from the anterior pituitary gland. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in the brain. There is also evidence that CRF plays a significant role in integrating the response in the immune system to physiological, psychological, and immunological stressors.

CRF has been implicated in psychiatric disorders and neurological diseases including depression and anxiety, as well as the following conditions: Alzheimer's disease, Huntington's disease, progressive supranuclear palsy, amyotrophic lateral sclerosis, Parkinson's disease, epilepsy, migraine, alcohol and substance abuse and associated withdrawal symptoms, obesity, metabolic syndrome, congenital adrenal hyperplasia, Cushing's disease, hypertension, stroke. irritable bowel syndrome, stress-induced gastric ulceration, premenstrual syndrome, sexual dysfunction, premature labor, inflammatory disorders, allergies, multiple sclerosis, visceral pain, sleep disorders, pituitary tumors or ectopic pituitary-derived tumors, chronic fatigue syndrome and fibromyalgia.

CRF receptor subtypes, CRF1 and CRF2, have been identified and are distributed heterogeneously within the brain thereby suggesting potential functional diversity. For example, widely distributed brain CRF1 receptors are strongly implicated in emotionality accompanying exposure to environmental stressors. Significantly, CRF1, not CRF2, receptors appear to mediate select anxiogenic like behaviors. A more discrete septal/hypothalmic distribution and the availability of alternative endogenous ligands suggest a different functional role for the CRF2 receptor. For example, a novel CRF-family neuropeptide with preferential affinity for CRF2 relative to CRF1 receptors is reported to suppress appetite without producing the profile of behavioral activation observed with selective CRF1 agonism. In other cases, CRF2 agonism produces similar effects to those reported for CRF1 antagonists or CRF1 gene deletion. For example, while CRF2 agonists have been proposed as antiobesity agents, CRF1 antagonists may be an important treatment for obesity as well.

Certain pyrrolo[2,3-d]pyrimidines, pyrrolo[3,2-d]pyrimidines, pyrazolo[1,5-a]pyrimidines, 1,2,3-triazolo[4,5-b]pyridines, and pyrazolo[1,5-a]-1,3,5-triazines, useful as CRF antagonists, are described in WO 94/13676, WO 97/29109, WO 98/08847, and WO 98/03510.

The present invention provides novel thiophene pyrazolopyrimidines useful as CRF1 receptor antagonists. In view of the above, it is desirable to discover new efficacious and selective antagonists of CRF1 as potentially valuable therapeutic agents for the treatment of psychiatric and neuroendocrine disorders, neurological diseases, and metabolic syndrome. Further, since a majority of commercial CNS and cardiovascular drugs exhibit undesirable bioavailability profiles, it is also desirable to discover new compounds with superior bioavailability profiles relative to known CRF antagonists such as CP154526 and NBI30775.

SUMMARY OF THE INVENTION

In one embodiment, the present invention relates to a compound of Formula I wherein:

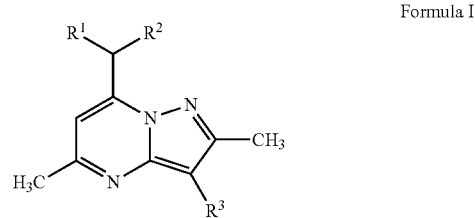

Formula I $R^1$ and $R^2$ are independently hydrogen or $C_1$-$C_3$alkyl;
$R^3$ is

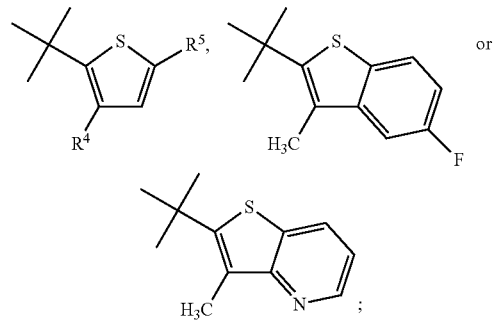

$R^4$ is Cl or methyl;
$R^5$ is hydrogen, Br, nitro, methoxy, methoxymethyl, dimethylamino, ethoxycarbonyl, acetamido, acetoxy,

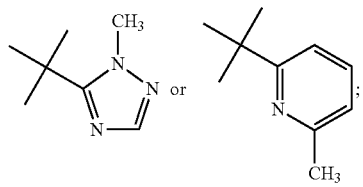

or a pharmaceutically acceptable salts thereof.

In another embodiment, the present invention relates to a method of treating depression or major depressive disorder, anxiety, alcohol or substance abuse, obesity, hypertension, metabolic syndrome, irritable bowel syndrome, epilepsy, stroke, sleep disorders, allergy, migraine, premenstrual syndrome (PMS), infertility, sexual dysfunction, congenital adrenal hyperplasia, Cushing's disease, premature labor, stress-induced gastric ulceration, inflammatory disorders, pituitary or ectopic pituitary-derived tumors, chronic fatigue syndrome, fibromyalgia, visceral pain or multiple sclerosis in a patient, comprising: administering to a patient in need thereof a therapeutically effective amount of a compound of Formula I, or a pharmaceutically acceptable salt thereof.

In another embodiment, the present invention relates to use of a compound of Formula I, or a pharmaceutically acceptable salt thereof, for the manufacture of a medicament for the treatment of depression or major depressive disorder, anxiety, alcohol or substance abuse, obesity, hypertension, metabolic syndrome, irritable bowel syndrome, epilepsy, stroke, sleep disorders, allergy, migraine, premenstrual syndrome (PMS), infertility, sexual dysfunction, congenital adrenal hyperplasia, Cushing's disease, premature labor, stress-induced gastric ulceration, inflammatory disorders, pituitary or ectopic pituitary-derived tumors, chronic fatigue syndrome, fibromyalgia, visceral pain or multiple sclerosis.

In another embodiment, the present invention relates to a compound of Formula I, or a pharmaceutically acceptable salt thereof, for use as a pharmaceutical.

DETAILED DESCRIPTION OF THE INVENTION

As used above, and throughout the description of the invention, the following terms, unless otherwise indicated, shall be understood to have the following meanings:

"Alkyl" means a saturated aliphatic hydrocarbon group, which may be straight or branched, having 1 to 5 carbon atoms in the chain.

"Pharmaceutically acceptable excipient" refers to a pharmaceutically acceptable formulation carrier, solution, or additive to enhance the formulation characteristics. Such excipients must be compatible with the other ingredients of the formulation and not deleterious to the recipient thereof and are well known to the skilled artisan (see e.g. *Remingtons Pharmaceutical Sciences*, 19$^{th}$ Edition, Mack Publishing Company, 1995).

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed (see e.g. *Remingtons Pharmaceutical Sciences*, 19$^{th}$ Edition, Mack Publishing Company, 1995).

"Therapeutically effective amount" or "effective amount" means the amount of the compound of formula I of the present invention or pharmaceutical composition containing a compound of formula I of the present invention that will elicit the biological or medical response of or desired therapeutic effect on a tissue, system, animal or human that is being sought by the researcher, veterinarian, medical doctor or other clinician.

The terms "treatment," "treat," "treating," and the like, are meant to include both slowing and reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed. The term "treatment" and like terms also include preventive (e.g., prophylactic) and palliative treatment. Prevention of the disease is manifested by a prolonging or delaying of the onset of the symptoms of the disease.

The symbol "—" in a molecular structure indicates the position of attachment for that particular substituent.

When any variable occurs more than one time in any constituent or in formula I, its definition on each occurrence is independent of its definition at every other occurrence. Also, combinations of substituents and/or variables are permissible only if such combinations result in stable compounds. In choosing compounds of the present invention, one of ordinary skill in the art will recognize that the various substituents, i.e. $R^1$, $R^2$, etc., are to be chosen in conformity with well-known principles of chemical structure connectivity.

Under standard nomenclature used throughout this disclosure, the terminal portion of the designated side chain is described first, followed by the adjacent functionality toward the point of attachment. For example, an arylcarbonylaminoalkyl substituent is equivalent to aryl-C(O)—NH-alkyl-.

The present invention contemplates specific classes of inventions, such as the following:

(a) A compound of Formula I, or a pharmaceutically acceptable salt thereof,
wherein $R^1$ and $R^2$ are independently ethyl or n-propyl;

(b) A compound of Formula I, or a pharmaceutically acceptable salt thereof,
wherein $R^3$ is

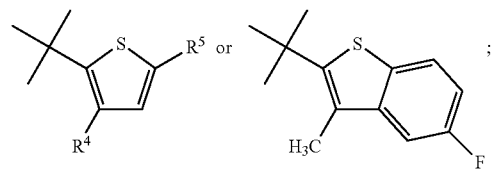

(c) A compound of Formula I, or a pharmaceutically acceptable salt thereof,
wherein $R^5$ is methoxy, methoxymethyl, dimethylamino or

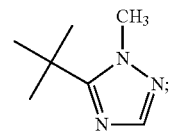

(d) Use of a compound of Formula I, or a pharmaceutically acceptable salt thereof, for treating depression or anxiety;

(e) Use of a compound of Formula I, or a pharmaceutically acceptable salt thereof, for treating alcohol or substance abuse;

(f) A compound of Formula I, or a pharmaceutically acceptable salt thereof, exhibiting a Ki value for CRF1 binding of ≦500 nM;

(g) A compound of Formula I, or a pharmaceutically acceptable salt thereof, exhibiting a Ki value for CRF1 binding of ≦50 nM;

(h) A compound of Formula I, or a pharmaceutically acceptable salt thereof, exhibiting a Ki value for CRF1 binding of ≦5 nM;

(i) A compound of Formula I, or a pharmaceutically acceptable salt thereof, exhibiting a Ki value for CRF1 binding of ≦500 nM and selectively binding to CRF1 (i.e., lower Ki) relative to CRF2;

(j) A compound of Formula I, or a pharmaceutically acceptable salt thereof, exhibiting a Ki value for CRF1 binding of ≦50 nM and selectively binding to CRF1 (i.e., lower Ki) relative to CRF2; and (k) A compound of Formula I, or a pharmaceutically acceptable salt thereof, exhibiting a Ki value for CRF1 binding of ≦5 nM and selectively binding to CRF1 (i.e., lower Ki) relative to CRF2;

(l) A compound of Formula I, or a pharmaceutically acceptable salt thereof, with a superior bioavailability profile relative to known CRF antagonists (e.g., CP154526 and NBI30775).

The compounds of the present invention are preferably formulated as pharmaceutical compositions administered by a variety of routes. Preferably, such compositions are for oral administration. Such pharmaceutical compositions and processes for preparing same are well known in the art (See, e.g., *Remington: The Science and Practice of pharmacy*, A. Gennaro, et al., eds., 19th ed., Mack Publishing Co., 1995).

The compounds of Formula I are generally effective over a wide dosage range. For example, dosages per day normally fall within the range of about 0.0001 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

The compounds of Formula I are CRF-1 antagonists and, as such, are useful for treating a condition which is treatable by reducing CRF1 receptor stimulation. Corticotropin releasing factor (CRF), a 41 amino acid peptide that is the primary physiological regulator of proopiomelanocortin (POMC) derived peptide secretion from the anterior pituitary gland [J. Rivier et al., *Proc. Natl. Acad. Sci.* (*USA*) 80:4851 (1983); W. Vale et al., *Science* 213:1394 (1981)], has been linked to a number of medical conditions. For example, in addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in the brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is also evidence that CRF plays a significant role in integrating the response in the immune system to physiological, psychological, and immunological stressors [see, e.g., J. E. Blalock, *Physiological Reviews* 69:1 (1989); J. E. Morley, *Life Sci.* 41:527 (1987)].

CRF is involved in psychiatric disorders and neurological diseases including depression and anxiety [D. M. Nielsen, *Life Sci.* 78:909-919; H. E. Kunzel et al., *J. Psychiatr. Res.* 37:525-533; D. R. Gehlert et al., *Eur. J. Pharmacol.* 509:145-153]. A role for CRF has also been postulated in the etiology and pathophysiology of Alzheimer's disease, Huntington's disease, progressive supranuclear palsy and amyotrophic lateral sclerosis, as they relate to the dysfunction of CRF neurons in the central nervous system [for a review, see: E. B. De Souze, *Hosp. Practice* 23:59 (1988)]. Chronic administration of CRF has been shown to produce impairment of the dopamine system suggesting a role in Parkinson's disease [E. Izzo et al., *Pharmacol. Biochem. Behav.* 81:701-708 (2005)]. Other neurological disorders in which CRF is involved include epilepsy [T. Z. Baram et al., *Brain Res.* 770:89-95 (1997)] and migraine [T. C. Theoharides et al., *Endocrinology* 136:5745-5750 (1995)]. CRF has been implicated in alcohol and substance abuse and associated withdrawal symptoms [D. H. Overstreet et al., *Pharmacol. Biochem. Behav.* 77:405-413; Y. Shaham et al., *Psychopharmacology* (Berl) 137:184-190]. Moreover, there is evidence that CRF has a role in various endocrine disorders and cardiovascular diseases such as obesity [E. Timofeeva and D. Richard, *Neuroendocrinology* 66:327-340 (1997)], metabolic syndrome [A. M. Ward et al., *Metabolism* 53:720-726 (2004)], congenital adrenal hyperplasia [D. P. Merke and G. B. Cutler Jr., *Endocrinol. Metab. Clin. North Am.* 30:121-135 (2001)], Cushing's disease [M. Labeur et al., *Curr. Drug Targets Immune Endocr. Metabol. Disord.* 4:335-342 (2004)], hypertension [R. J. Briscoe, et al., *Brain Res.* 881:204-207 (2000)], and stroke [S. L. Stevens et al., *J. Cereb. Blood Flow Metab.* 23:1151-1159 (2003)]. Gastric disturbances such as irritable bowel syndrome [Y. Tache et al., *Eur. J. Surg. Suppl:*16-22 (2002)] and stress-induced gastric ulceration [K. E. Gabry et al., *Mol. Psychiatry.* 7:474-483, 433 (2002)] have been shown to be related to CRF. In addition, there is indication that CRF has a role in various areas of human female health, for example, premenstrual syndrome [F. Facchinetti et al., *Psychosom. Med.* 56:418-422 (1994)], infertility [L. Ghizzoni et al., Endocrinology 138: 4806-4811 (1997)], sexual dysfunction [J. E. Jones et al., *Am. J. Physiol. Regul. Integr. Comp. Physiol.* 283:R591-597 (2002)], and premature labor [P. D. Wadhwa et al., *Am. J. Obstet. Gynecol.* 191:1063-1069 (2004)]. There is also evidence that CRF has a significant role in the immune system indicating therapeutic potential for treating inflammatory disorders [A. Gravanis and A. N. Margioris, *Curr. Med. Chem.* 12:1503-1512 (2005)], allergies [L. K. Singh. et. al., *Brain Behav. Immun.* 13:225-239 (1999)], multiple sclerosis and other autoimmune disorders [C. Benou et al., *J. Immunol.* 174:5407-5413 (2005)]. In addition to the preceding, CRF has been implicated in visceral pain [M. Nijsen et al., *Neurogastroenterol. Motil.* 17:423-432 (2005)], sleep disorders [T. M. Buckley and A. F. Schatzberg, *J. Clin. Endocrinol. Metab.* 90:3106-3114 (2005)], pituitary tumors or ectopic pituitary-derived tumors [K. D. Dieterich et al., *J. Clin. Endocrinol. Metab.* 83:3327-3331 (1998)], chronic fatigue syndrome and fibromyalgia [G. Neeck and L. J. Crofford, *Rheum. Dis. Clin. North Am.* 26:989-1002 (2000)].

CRF receptor subtypes, CRF1 and CRF2, have been identified and are distributed heterogeneously within the brain [D. T. Chalmers et al., *TIPS* 17:166-72 (1996)] thereby suggesting potential functional diversity [S. C. Heinrichs et al., *Regul. Peptides* 71:15 (1997)]. For example, widely distributed brain CRF1 receptors are strongly implicated in emotionality accompanying exposure to environmental stressors [G. Liebsch et al., *Regul. Peptides* 59: 229-39 (1995); D. W. Schulz, *PNAS* 93: 10477-82 (1996)]. Significantly, CRF1, not CRF2, receptors appear to mediate select anxiogenic like behaviors [Heinrichs et al., 1997]. A more discrete septal/hypothalmic distribution [D. T. Chalmers et al., *J. Neurosci.* 15(10): 6340-50 (1995)] and the availability of alternative endogenous ligands [J. Vaughan et al., *Nature* 378: 287-92 (1995)] suggest a different functional role for the CRF2 receptor [Heinrichs et al., 1997]. For example, a novel CRF-family neuropeptide with preferential affinity for CRF2 relative to CRF1 receptors is reported to suppress appetite without producing the profile of behavioral activation observed with selective CRF1 agonism (H. Tezval et al., *PNAS* 101 (25): 9468-9473 (2004)]. In some cases, CRF2 agonism pro duces similar effects to those reported for CRF1 antagonists or CRF1 gene deletion [S. C. Heinrichs, *Trends in Pharmacological Sciences* 20(8):311-5 (1999)]. For example, while CRF2 agonists have been proposed as antiobesity agents, CRF1 antagonists may be an important treatment for obesity as well [C. Contoreggi et al., *Neuroendocrinology* 80(2):111-23 (2004)].

Preparing Compounds of the Invention

All of the compounds of the present invention can be chemically prepared, for example, by following the synthetic routes set forth in the Schemes below. However, the following discussion is not intended to be limiting to the scope of the present invention in any way. For example, the specific synthetic steps for each of the routes described may be combined in different ways, or in conjunction with steps from different schemes, to prepare additional compounds of Formula (I). The products of each step can be recovered by conventional methods including extraction, evaporation, precipitation, chromatography, filtration, trituration, crystallization, and the like. In the Schemes below all substituents, unless otherwise indicated, are as previously defined and suitable reagents are well known and appreciated in the art.

Formation of a compound of formula (I) can be carried out in accordance with reactions as depicted in Scheme 1. An appropriate compound of formula (I) is one in which $R^1$, $R^2$, $R^3$, $R^4$, and $R^5$ are as defined for Formula I.

In Step 1, ethyl acetoacetate and 5-methyl-2H-pyrazol-3-ylamine are condensed to form 2,5-dimethyl-4H-pyrazolo[1,5-a]pyrimidine-7-one (1) in refluxing acetic acid.

The pyrazolo[1,5-a]pyrimidine-7-one of formula (1) is subsequently converted to 7-chloro-2,5-dimethyl-pyrazolo[1,5-a]pyrimidine in Step 2 using phosphorous oxychloride and dimethylaniline in an inert solvent, such as toluene, at the reflux temperature of the solvent.

In Scheme 1, Step 3, a Grignard reagent of formula (3) (X=Cl or Br) is reacted with the chloride of formula (2), in an inert solvent such as toluene, at reflux temperature to provide the 7-alkyl pyrazolopyrimidine of formula (4). Alternatively the 7-alkyl pyrazolopyrimidine of formula (4) is obtained by condensation of a diketone with 5-methyl-2H-pyrazol-3-ylamine as shown in Step 4. The reaction is performed in ethanol with a catalytic amount of piperidine at a temperature of 60 to 80° C. (Novinson, T., et. al. *J. Med. Chem.* 1975, 18, 460). When $R^1$=H a mixture of regioisomers are obtained, for example when $R^2$=propyl, which are separated after the iodination of Step 5.

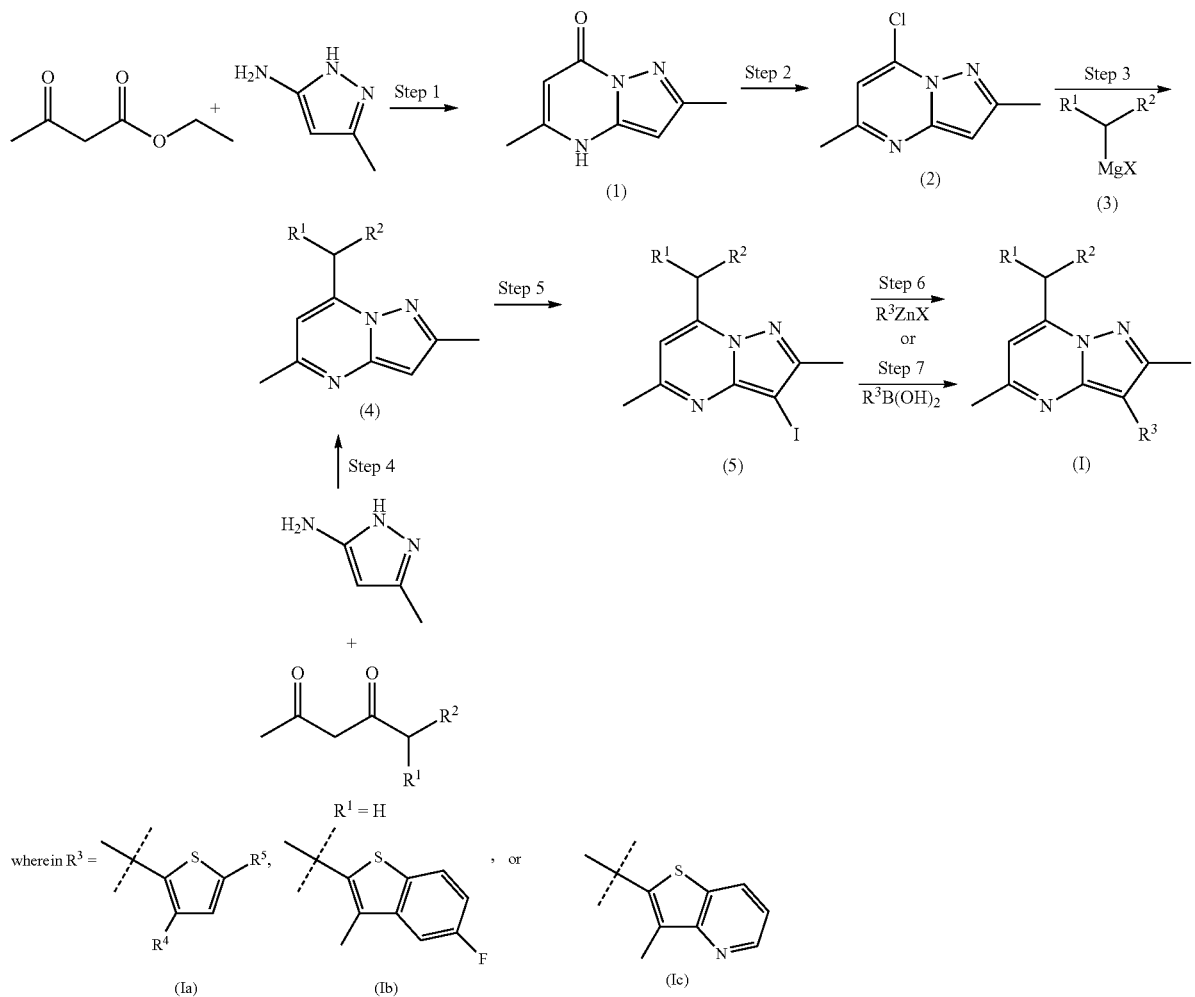

Scheme 1

The pyrazolopyrimidine of formula (4) is functionalized to an iodo pyrazolopyrimidine of formula (5) in Step 5 using an excess of N-iodosuccinimide in acetonitrile.

In Scheme 1, Step 6, the iodo pyrazolopyrimidine of formula (5) is reacted with a heterocyclic zinc halide ($R^3ZnX$) (X=Cl or Br) in a Negishi cross-coupling reaction. The heterocyclic zinc halide can be generated using methods well known to those skilled in the art. For example, the organozinc reagent is generated by reacting the heterocyclic bromide with zinc metal or, alternatively, using the non-halogenated heterocycle to form the heterocyclic lithium reagent with n-, sec-, or tert-butyl lithium, followed by lithium-zinc exchange with $ZnCl_2$. The organozinc reagent is coupled with the iodo pyrazolopyrimidine of formula (5) in the presence of a palladium catalyst, for example, dichloro[1,1'-bis(diphenyl-phosphino)ferrocene]palladium (II) dichloromethane, in an inert solvent, such as THF, at reflux temperature for about 12 to 36 hours to provide a pyrazolopyrimidine of formula (I).

As will be readily appreciated, heteroaryl boronic acids can be prepared by methods similar to those described herein using procedures that are well-known in the art. For example, thiophenes and benzothiophenes can be brominated using N-bromosuccinimide and subsequently converted to the boronic acid using halogen metal exchange with an alkyl lithium reagent followed by treatment with trimethylborate and hydrolysis upon workup.

It will be appreciated by one skilled in the art that a thienopyridine, for example, as in a compound of formula (Ic), is readily obtained by conversion of the commercially available thieno[3,2-b]pyridin-7-ol to the bromide followed by halogen metal exchange and quenching with a proton source such as methanol/water. Subsequent bromination with bromine at the 3-position followed by Suzuki coupling with methylboronic acid provides 3-methyl-thieno[3,2-b]pyridine which is coupled with an iodo pyrazolopyrimidine of formula (5) using $ZnCl_2$ as described above.

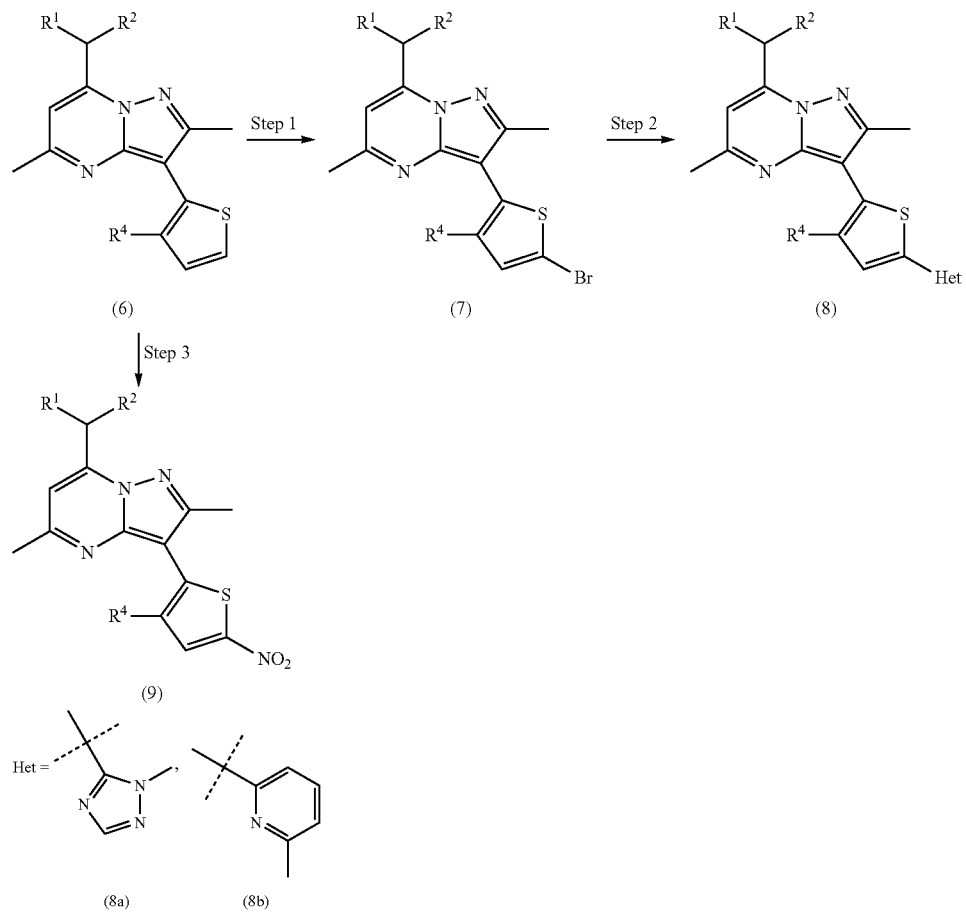

Scheme 2

Alternatively, in Step 7, a heterocyclic boronic acid ($R^3B(OH)_2$) is used in a Suzuki coupling reaction with the iodo compound of formula (5). There are numerous reaction conditions available to the skilled artisan for this coupling procedure. The preferred conditions use a solvent mixture of toluene/ethanol/2 M sodium carbonate with a palladium catalyst, for example, bis(tri-t-butylphosphine)palladium(0), at 60° C. to reflux temperature, for about 12 to 36 hours.

Formation of a compound of formula (7), (8), or (9) can be carried out in accordance with reactions as depicted in Scheme 2. An appropriate compound of formula (7), (8), or (9) is one in which $R^1$, $R^2$, and $R^4$ are as defined for formula I and "Het" is defined as shown.

In Scheme 2, Step 1, a thiophene of formula (6) is brominated with N-bromosuccinimide in an inert solvent such as dichloromethane or chloroform.

In Step 2, a bromothiophene of formula (7) is coupled with a heterocyclic zinc reagent to provide a thiophene heterocycle of formula (8). The heterocyclic zinc reagent is formed from the bromoheterocycle and zinc metal, and reacted in situ with a bromothiophene of formula (7). The reaction is performed in an inert solvent, such as THF, at the reflux temperature of the solvent. Alternatively, a heterocyclic lithium reagent can be formed for example, using n-, sec-, or tert-butyl lithium with 1-methyl-1,2,4-triazole followed by lithium-zinc exchange with $ZnCl_2$ to obtain the heterocyclic zinc reagent.

In Scheme 2, Step 3, a thiophene of formula (6) is nitrated to give a nitrothiophene of formula (9). Preferred conditions use a solvent mixture of dichloromethane and TFA with 70% nitric acid. It will be appreciated by one skilled in the art that the nitrothiophene of formula (9) can serve as an intermediate for further functionalization. For example, the nitro group can be reduced and acylated to give the acetamide or alkylated to give the dialkylamine.

Also, it is recognized that the steps required to prepare a compound of formula (8) can be carried out in any order, such that the 2-heterocycle thiophene can be prepared using methods known in the art, and then functionalized as a bromothiophene or thiophenyl boronic acid and then coupled with an iodo pyrazolopyrimidine of formula (5).

Scheme 3

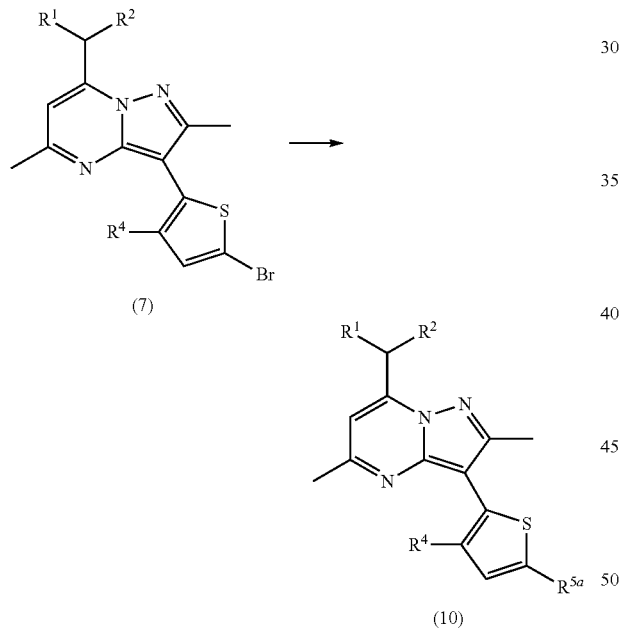

Formation of a compound of formula (10) can be carried out in accordance with reactions as depicted in Scheme 3. An appropriate compound of formula (10) is one in which $R^1$, $R^2$, and $R^4$ are as defined for formula I and $R^{5a}$=—$OCH_3$, —OC(O)$CH_3$, —$CH_2OCH_3$, or —$CO_2CH_2CH_3$.

As will be readily appreciated a bromothiophene of formula (7) represents a useful intermediate which can be easily transformed into a variety of substituted thiophenes by the skilled artisan. For example, formation of the thienyl Grignard reagent followed by treatment with oxygen (Hurd, C. D. and Kreuz, K. *JACS* 1950, 72, 5543) provides a 2-hydroxy thiophene which is acylated to provide the acetoxy derivative. Said Grignard reagent can also be treated with an electrophile, such as ethylcyanoformate to provide an ethoxycarbonyl substituted thiophene. Halogen-lithium exchange with n-, sec-, or tert-butyl lithium can provide a thienyl lithium reagent, which can be subsequently reacted with electrophiles, such as alkylhalides, like iodomethyl methylether. In addition treatment with copper oxide, sodium iodide, and sodium methoxide provides a 2-methoxy thiophene.

As used herein, "TLC" refers to thin layer chromatography; "HPLC" refers to high performance liquid chromatography; "δ" refers to part per million down-field from tetramethylsilane; "THF" refers to tetrahydrofuran; "EtOAc" refers to ethyl acetate; "HOAc" refers to acetic acid; "MeOH" refers to methanol; "DME" refers to dimethoxyethane.

EXAMPLES

Without further elaboration, it is believed that one skilled in the art can, using the preceding description, practice the present invention to its fullest extent. The following preparations and examples are provided to describe the invention in further detail. They are intended to illustrate and not to limit the invention in any way whatsoever. The reagents and starting materials are readily available to, or may be readily synthesized by, one of ordinary skill in the art. Examples 1-27 provide representative compounds and illustrate the preparation thereof. Examples A-C illustrates various biological assays that can be used for determining the biological properties of the compounds of the invention. Those skilled in the art will promptly recognize appropriate variations from the procedures described in the examples. The names of the compounds of the present invention are provided by ChemDraw Ultra® version 7.0.1.

Preparation 1

2,5-Dimethyl-4H-pyrazolo[1,5-a]pyrimidin-7-one

Add ethyl acetoacetate (128 g, 0.98 mol) dropwise to an acetic acid solution (500 mL) of 5-methyl-2H-pyrazol-3-ylamine (100 g, 0.95 mol), keeping the temperature at 25-28° C. Heat the mixture at reflux for 10 h and then cool to room temperature. Add the reaction to tert-butyl methyl ether (5 L) cooled to 5° C., keeping the temperature below 10° C. Stir for 1 h at 5° C., and filter. Dry the resulting material in vacuo overnight to provide a white solid (158 g, 96%).

Preparation 2

7-Chloro-2,5-dimethyl-pyrazolo[1,5-a]pyrimidine

To a suspension of 2,5-dimethyl-4H-pyrazolo[1,5-a]pyrimidin-7-one (10.0 g, 61.3 mmol) in toluene (150 mL), add N,N-dimethylaniline (9.7 mL, 76.7 mmol). Add phosphorus oxychloride (11.2 mL, 122.6 mmol) dropwise to this white suspension. Reflux for 3 h under an inert atmosphere, cool to room temperature, and concentrate the reaction to a brown oil using reduced pressure. Dissolve the oil in ethyl acetate (250 mL) and basify with 1 N NaOH. Separate and extract the basic aqueous phase with additional ethyl acetate (2×100 mL). Combine the organic phases, dry over anhydrous magnesium sulfate, filter, and concentrate under reduced pressure to yield a brown solid. Purify the material using flash chromatography, eluting with 80% hexane/20% (30% THF/hexane) to 0% hexane/100% (30% THF/hexane) in a step gradient of 20% increments to provide a light green solid (6.65 g, 59%). ES/MS m/z ($^{35}$Cl) 182.3 (M+1)$^+$.

Preparation 3

7-(1-Ethyl-propyl)-2,5-dimethyl-1pyrazolo[1,5-a]pyrimidine

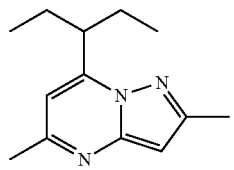

Charge an oven dried flask, fitted with a reflux condenser, with a catalytic amount of iodine and Rieke® magnesium (1.0 M in THF, 52 mL, 52 mmol) under an inert atmosphere. Heat to 45° C. and add 3-bromopentane (5.3 mL, 42.9 mmol) to the reaction. The temperature spikes as the Grignard reaction is initiated. Stir the reaction an additional 4 h at 50° C. and cool to room temperature. Allow the magnesium metal to settle and canulate off the Grignard reagent under positive argon pressure into a flask containing 7-chloro-2,5-dimethylpyrazolo[1,5-a]pyrimidine (5.19 g, 28.6 mmol) in anhydrous toluene (50 mL). Heat to reflux under an inert atmosphere for 48 h. Cool the reaction to room temperature and quench with water. Dilute the reaction with ethyl acetate (150 mL) and add water (50 mL). Separate and extract the aqueous phase with ethyl acetate (75 mL). Combine the organic phases, dry over anhydrous magnesium sulfate and concentrate under reduced pressure. Purify using flash chromatography, eluting with 80% pentane/20% (30% THF/pentane) to 0% pentane/100% (30% THF/pentane) in a step gradient of 20% increments to give a yellow oil (2.59 g, 42%). ES/MS m/z 218.1 (M+1)$^+$.

Prepare the following compounds essentially as described in Preparation 3, using the commercially available Grignard reagent or preparing the Grignard reagent as described above.

| Prep. No. | Chemical name | Physical data: NMR or MS (m/z) |
|---|---|---|
| 4 | 7-(1-Propyl-butyl)-2,5-dimethyl-pyrazolo[1,5-a]pyrimidine | 246.3 (M + 1)$^+$ |
| 5 | 7-Isopropyl-2,5-dimethyl-pyrazolo[1,5a]pyrimidine | $^1$H NMR (400 MHz, CDCl$_3$): 6.41 (s, 1H), 6.30 (s, 1H), 3.81-3.77 (m, 1H), 2.52 (s, 3H), 2.47 (s, 3H), 1.37 (d, J = 7.0 Hz, 6H) |

Preparation 6

7-Butyl-2,5-dimethyl-pyrazolo[1,5-a]pyrimidine

Add 5-methyl-2H-pyrazol-3-ylamine (217 mg, 2.17 mmol), nonane-2,4-dione (339 mg, 2.39 mmol) and piperidine (1 drop) to ethanol (10 mL) and heat at 80° C. overnight. Cool to room temperature and concentrate to dryness. Purify by silica gel column chromatography (0-20% ethyl acetate in hexane) to obtain a mixture of two isomers (2 g).

Preparation 7

7-(1-Ethyl-propyl)-3-iodo-2,5-dimethyl-pyrazolo[1,5-a]pyrimidine

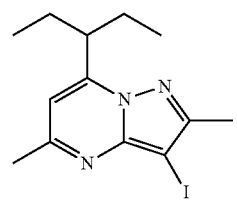

Dissolve 7-(1-ethyl-propyl)-2,5-dimethyl-pyrazolo[1,5-a]pyrimidine (2.14 g, 9.84 mmol) in anhydrous acetonitrile (25 mL) and add 6 portions (0.5 g each) of N-iodosuccinimide (3.0 g, 13.3 mmol) at 10 min intervals. Stir the reaction for 4 h. Strip off the acetonitrile and dilute the resulting oil with dichloromethane (100 mL). Wash the orange solution with saturated ammonium chloride solution (2×50 mL). Collect the organic phase, dry over anhydrous magnesium sulfate, filter, and concentrate under reduced pressure to yield a dark red oil. Purify using flash chromatography, eluting with 100% pentane/0% (20% ethyl acetate/pentane) to 0% pentane/100% (20% ethyl acetate/pentane) in a step gradient of 50% increments to give an orange oil (3.28 g, 97%). $^1$H NMR (400 MHz, CDCl$_3$): 6.44 (s, 1H), 3.59 (m, 1H), 2.61 (s, 3H), 2.49 (s, 3H), 1.86-1.76 (m, 4H), 0.85 (t, J=7.5 Hz, 6H).

Prepare the following compounds essentially as described in Preparation 7.

| Prep. No. | Chemical name | Physical data: NMR or MS (m/z) |
|---|---|---|
| 8 | 7-(1-Propyl-butyl)-3-iodo-2,5-dimethyl-pyrazolo[1,5-a]pyrimidine | $^1$H NMR (400 MHz, CDCl$_3$): 6.42 (s, 1H), 3.74-3.70 (m, 1H), 2.58 (s, 3H), 2.46 (s, 3H), 1.74-1.68 (m, 4H), 1.28-1.14 (m, 4H), 0.84 (t, J = 7.0 Hz, 6H). |
| 9 | 7-Isopropyl-3-iodo-2,5-dimethyl-pyrazolo[1,5a]pyrimidine | 316.0 (M + 1)$^+$ |
| 10* | 7-Butyl-3-iodo-2,5-dimethyl-pyrazolo[1,5-a]pyrimidine | 330 (M + 1)$^+$ |

*Workup: wash organics with Na$_2$S$_2$O$_3$ aqueous solution. Perform reaction on mixture of isomers from Preparation 6. Separate the two isomers on silica gel (0-20% EtOAc/hexane).

Example 1

3-(3-Chloro-thiophene-2-yl)-7-(1-ethyl-propyl)-2,5-dimethyl-pyrazolo[1,5-a]pyrimidine

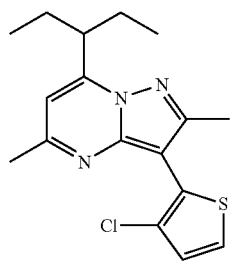

Suspend Reike® zinc (5 g/100 mL THF, 20 mL, 15.0 mmol) in anhydrous THF (10 mL) and add 2-bromo-3-chlorothiophene (1.98 g, 10.0 mmol). Reflux the mixture under an inert atmosphere in an oil bath (85° C.) for 3 h. Cool the reaction to room temperature and centrifuge the remaining zinc metal. Canulate off the reagent solution into a new vessel under positive argon pressure and add 7-(1-ethyl-propyl)-3-iodo-2,5-dimethyl-pyrazolo[1,5-a]pyrimidine (1.72 g, 5.0 mmol). Degas the solution by positive argon pressure for 10-15 min and add dichloro[1,1'-bis(diphenyl-phosphino)ferrocene]palladium (II) dichloromethane (0.225 g, 0.275 mmol). Stir at reflux temperature overnight under an inert atmosphere. Cool the reaction to room temperature, quench with saturated ammonium chloride, and dilute with ethyl acetate (75 mL). Separate and extract the aqueous portion with ethyl acetate (50 mL), combine the organic phases, dry over anhydrous magnesium sulfate, filter, and concentrate under reduced pressure. Purify the resulting residue using flash chromatography, eluting with 100% hexane/0% (15% ethyl acetate/hexane) to 0% hexane/100% (15% ethyl acetate/hexane) in a step gradient of 10% increments to give a yellow solid (1.35 g, 40%). ES/MS m/z ($^{35}$Cl) 334.4 (M+1)$^+$.

Prepare the following compounds essentially as described in Example 1.

| Ex. No. | Chemical name | MS (m/z) |
|---|---|---|
| 2 | 3-(3-Chloro-thiophene-2-yl)-7-(1-propyl-butyl)-2,5-dimethyl-pyrazolo[1,5-a]pyrimidine, | ($^{35}$Cl) 362.0 (M + 1)$^+$ |
| 3 | 3-(3-Chloro-thiophene-2-yl)-7-isopropyl-2,5-dimethyl-pyrazolo[1,5-a]pyrimidine | ($^{35}$Cl) 306.0 (M + 1)$^+$ |

Example 4

3-(3-Methyl-thiophene-2-yl)-7-(1-ethyl-propyl)-2,5-dimethyl-pyrazolo[1,5-a]pyrimidine Charge an oven dried flask with 3-methyl-2-thienylzinc bromide (11.0 mL, 5.5 mmol), anhydrous THF (6.0 mL) and 7-(1-ethyl-propyl)-3-iodo-2,5-dimethyl-pyrazolo[1,5-a]pyrimidine (0.536 g, 1.56 mmol). Degas for 10-15 min with positive argon pressure and add dichloro[1,1'-bis(diphenylphosphino)ferrocene]palladium (II) dichloromethane (0.12 g, 0.15 mmol). Reflux overnight in an oil bath (100° C.) under an inert atmosphere. Cool the reaction to room temperature, quench with saturated ammonium chloride, and dilute with ethyl acetate (75 mL). Separate and extract the aqueous portion with ethyl acetate (50 mL). Combine the organic phases, dry over anhydrous magnesium sulfate, filter, and concentrate under reduced pressure. Purify the resulting residue using flash chromatography, eluting with 100% pentane/0% (25% ethyl acetate/pentane) to 0% pentane/100% (25% ethyl acetate/pentane) in a step gradient of 10% increments to give a white foam. Triturate with hexane and filter. (0.432 g, 8%). $^1$H NMR (400 MHz, CDCl$_3$): 7.26 (d, J=4.8, MHz, 1H), 6.96 (d, J=5.3 Hz, 1H), 6.42 (s, 1H), 3.64-3.60 (m, 1H), 2.53 (s, 3H), 2.43 (s, 3H), 2.14 (s, 3H), 1.87-1.79 (m, 4H), 0.88 (t, J=7.0 Hz, 6H).

Example 5

3-(5-Bromo-3-chloro-thiophene-2-yl)-7-(1-ethyl-propyl)-2,5-dimethyl-pyrazolo[1,5-a]pyrimidine

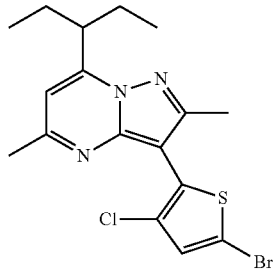

Dissolve 3-(3-chloro-thiophene-2-yl)-7-(1-ethyl-propyl)-2,5-dimethyl-pyrazolo[1,5-a]pyrimidine (1.16 g, 3.5 mmol) in dichloromethane (15 mL) and add N-bromosuccinimide (0.69 g, 3.85 mmol) in one aliquot. Stir 2 h under an inert atmosphere and confirm the reaction is complete using TLC. Dilute the reaction with dichloromethane (50 mL), wash with water (75 mL), brine (50 mL), dry over anhydrous magnesium sulfate, filter, and concentrate under reduced pressure to give a yellow solid (1.56 g, quantative yield). $^1$H NMR (400 MHz, DMSO): 7.39 (s, 1H), 6.88 (s, 1H), 3.48-3.44 (m, 1H), 2.45 (s, 3H), 2.39 (s, 3H), 1.80-1.73 (m, 4H), 0.76 (t, J=7.0 Hz, 6H).

Prepare the following compounds essentially as described in Example 5.

| Ex. No. | Chemical name | MS (m/z) |
|---|---|---|
| 6 | 3-(5-Bromo-3-chloro-thiophene-2-yl)-7-(1-propyl-butyl)-2,5-dimethyl-pyrazolo[1,5-a] pyrimidine | ($^{35}$Cl$^{81}$Br) 441.7 (M+) |
| 7* | 3-(5-Bromo-3-methyl-thiophene-2-yl)-7-(1-ethyl-propyl)-2,5-dimethyl-pyrazolo[1,5-a]pyrimidine | ($^{81}$Br) 393.8 (M + 1)$^+$ |
| 8* | 3-(5-Bromo-3-chloro-thiophene-2-yl)-7-isopropyl-2,5-dimethyl-pyrazolo[1,5-a] pyrimidine | ($^{35}$Cl$^{81}$Br) 385.0 (M+) |

*Purify by column chromatography eluting with hexanes/ethyl acetate.

Example 9

3-[3-Chloro-5-(2-methyl-2H-[1,2,4]triazole-3-yl)-thiophene-2-yl]-7-(1-ethyl-propyl)-2,5-dimethyl-pyrazolo[1,5-a]pyrimidine

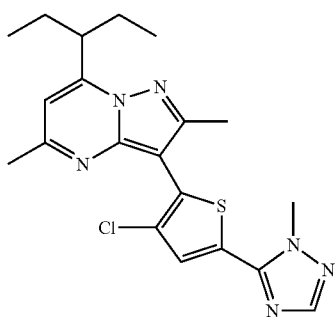

Suspend Reike® zinc (5 g/100 mL THF, 5.5 mL, 4.2 mmol) in anhydrous THF (5 mL) and add 1-methyl-5-bromo-1,2,4 triazole (0.4 g, 2.5 mmol). Reflux under an inert atmosphere in an oil bath (85° C.) for 3 h. Cool the reaction to room temperature and centrifuge the remaining zinc metal. Canulate off the reagent solution into a new vessel under positive argon pressure and add 3-(5-bromo-3-chloro-thiophene-2-yl)-7-(1-ethyl-propyl)-2,5-dimethyl-1pyrazolo[1,5-a]pyrimidine (0.64 g, 1.45 mmol). Degas the solution by positive argon pressure for 10-15 min and add dichloro[1,1-bis(diphenylphosphino)ferrocene]palladium (II) dichloromethane (0.136 g, 0.167 mmol). Reflux overnight under an inert atmosphere. Cool the reaction to room temperature, quench with saturated ammonium chloride, and dilute with ethyl acetate (75 mL). Separate and extract the aqueous portion with ethyl acetate (50 mL). Combine the organic phases, dry over anhydrous magnesium sulfate, filter, and concentrate under reduced pressure. Purify the resulting residue using flash chromatography, eluting with 100% hexane/0% (30% THF/hexane) to 0% hexane/100% (30% THF/hexane) in a step gradient of 10% increments to give a yellow solid (0.298 g, 50%). ES/MS m/z ($^{35}$Cl) 415.0 (M+1)$^+$.

Prepare the following compound essentially as described in Example 9, using commercially available 6-methyl-2-pyridylzinc bromide.

| Ex. No. | Chemical name | MS (m/z) |
|---|---|---|
| 10 | 3-[3-Cloro-5-(6-methyl-pyridin-2-yl)-thiophene-2-yl]-7-(1-ethyl-propyl)-2,5-dimethyl-pyrazolo[1,5-a]pyrimidine | ($^{35}$Cl) 424.8 (M + 1)$^+$ |

Example 11

3-(3-Chloro-5-methoxy-thiophene-2-yl)-7-(1-ethyl-propyl)-2,5-dimethyl-pyrazolo[1,5-a]pyrimidine Charge an oven dried flask with 3-(5-bromo-3-chloro-thiophene-2-yl)-7-(1-ethyl-propyl)-2,5-dimethyl-pyrazolo[1,5-a]pyrimidine (0.46 g, 1.1 mmol), copper oxide (0.045 g, 0.56 mmol), sodium iodide (0.020 g, 0.11 mmol), 25% sodium methoxide/methanol solution (10 mL) and anhydrous methanol (10 mL). Reflux the reaction in an oil bath (90° C.) over the weekend under an inert atmosphere. Quench the reaction with ice water and extract with ether (3×100 mL). Combine the organic portions, dry over anhydrous magnesium sulfate, filter, and concentrate under reduced pressure. Purify the resulting residue using flash chromatography, eluting with 100% hexane/0% (35% ethyl acetate/hexane) to 0% hexane/100% (35% ethyl acetate/hexane) in a step gradient of 10% increments to give a white foam (0.086 g, 21%). ES/MS m/z ($^{35}$Cl) 363.7 (M+1)$^+$.

Example 12

Acetic acid 4-chloro-5-[7-(1-ethyl-propyl)-2,5-dimethyl-pyrazolo[1,5-a]pyrimidin-3-yl]ester Add isopropyl bromide (0.25 mL, 2.7 mmol) to a suspension of 3-(5-bromo-3-chloro-thiophene-2-yl)-7-(1-ethyl-propyl)-2,5-dimethyl-1pyrazolo[1,5-a]pyrimidine (0.74, 1.8 mmol) in Reike® magnesium (1.0 M in THF, 2.7 mL, 2.7 mmol) and anhydrous THF (3 mL). Reflux under an inert atmosphere for 1 h and cool the reaction to room temperature. Bubble oxygen into the exothermic reaction under positive pressure at room temperature for 90 min. Quench the reaction with saturated ammonium chloride (30 mL), extract with ethyl acetate (2×100 mL), and concentrate under reduced pressure. Dissolve the oil in ether (150 mL), wash with 0.1 N sodium hydroxide (3×75 mL) and back extract the basic aqueous phase with ether (50 mL). Acidify the aqueous phase with saturated ammonium chloride and extract with dichloromethane (4×75 mL). Combine the dichloromethane portions, dry over anhydrous magnesium sulfate, filter, and concentrate under reduced pressure. Dissolve the crude oil (0.138 g, 0.39 mmol) in dichloromethane (2 mL) with triethylamine (0.23 mL, 1.6 mmol) and acetyl chloride (0.034 mL, 0.47 mmol). Stir under an inert atmosphere for 1 h, dilute with dichloromethane (50 mL), and wash with water (50 mL). Dry the organic phase over anhydrous magnesium sulfate, filter, and concentrate under reduced pressure. Purify the resulting residue using flash chromatography, eluting with 100% hexane/0% (25% ethyl acetate/hexane) to 0% hexane/100% (25% ethyl acetate/hexane) in a step gradient of 10% increments to give a white foam (0.084 g, 21%). ES/MS m/z ($^{35}$Cl) 392.0 (M+1)$^+$.

Example 13

3-(3-Chloro-5-methoxymethyl-thiophene-2-yl)-7-(1-ethyl-propyl)-2,5-dimethyl-1pyrazolo[1,5-a]pyrimidine Charge an oven dried flask with 3-(5-bromo-3-chloro-thiophene-2-yl)-7-(1-ethyl-propyl)-2,5-dimethyl-pyrazolo[1,5-a]pyrimidine (0.41, 1.0 mmol) and anhydrous THF (5 mL). Chill to −70° C. under an inert atmosphere and add n-butyl lithium (2.5 M hexane solution, 0.42 mL, 1.05 mmol). The yellow reaction turns dark red. Add iodomethyl methylether (0.09 mL, 1.10 mmol) and allow the reaction to warm to room temperature. Dilute the reaction mixture with ethyl acetate (100 mL), wash with water (75 mL), and brine (75 mL). Dry the organic portion over anhydrous magnesium sulfate and concentrate to an orange oil under reduced pressure. Purify the resulting residue using flash chromatography, eluting with 100% hexane/0% (20% ethyl acetate/hexane) to 0% hexane/100% (20% ethyl acetate/hexane) in a step gradient of 10% increments to give a yellow solid (0.107 g, 28%). ES/MS m/z ($^{35}$Cl) 378.3 (M+1)$^+$.

Example 14

4-Chloro-5-[7-(1-ethyl-propyl)-2,5-dimethyl-pyrazolo[1,5-a]pyrimidin-3-yl]-thiophene-2-carboxylic acid ethyl ester Chill to 0° C. a mixture of 3-(5-bromo-3-chloro-thiophene-2-yl)-7-(1-ethyl-propyl)-2,5-dimethylpyrazolo[1,5-a]pyrimidine (0.62 g, 1.5 mmol) in anhydrous THF (5 mL) under an inert atmosphere and add ethyl magnesium chloride (2 M THF solution, 0.83 mL, 1.65 mmol). Stir the reaction 5 min, warm to room temperature, and stir an additional 15 min before lowering the reaction temperature to 0° C. Add ethylcyanoformate (0.16 mL, 1.58 mmol) diluted in anhydrous THF (1 mL). Warm the reaction to room temperature and stir 1 h. Quench the reaction with saturated sodium bicarbonate (20 mL) and extract with ether (2×75 mL). Combine the organic portions, dry over anhydrous magnesium sulfate, filter, and concentrate under reduced pressure. Purify using flash chromatography, eluting with 100% hexane/0% (20% ethyl acetate/hexane) to 0% hexane/100% (20% ethyl acetate/hexane) in a step gradient of 10% increments. Dry the resulting material under vacuum to provide a white solid (0.114 g, 19%). ES/MS m/z ($^{35}$Cl) 406.3 (M+1)$^+$.

Preparation 11

2-(5-Bromo-4-methyl-thiophen-2-yl)-6-methyl-pyridine

Add 2.0 M lithium diisopropylamide (9.76 mL, 19.52 mmol) to a −78° C. solution of 2-bromo-3-methyl-thiophene (2.0 mL, 17.75 mmol) and THF (30 mL). After 45 minutes add ZnCl$_2$ (0.5 M in THF, 39.0 mL, 19.50 mmol) and stir the solution for 30 min. Add 2-bromo-6-methyl-pyridine (2.4 mL, 21.29 mmol) and Pd(PPh$_3$)$_4$ (0.50 g, 0.44 mmol). Warm the solution to ambient temperature and stir for 2 h. Wash the reaction with saturated NH$_4$Cl solution (20 mL). Wash the aqueous layer with CH$_2$Cl$_2$ (30 mL). Combine the organic layers, wash with saturated NH$_4$Cl solution (20 mL), dry over Na$_2$SO$_4$, filter and concentrate. Purify the resulting residue by silica gel column chromatography (10%-20% EtOAc/hexane gradient) to furnish the title compound (2.34 g, 49%). LC-ES/MS m/z ($^{79}$Br/$^{81}$Br) 267.7/269.5 (M+H)$^+$.

Preparation 12

3-Methyl-5-(6-methyl-pyridin-2-yl)-thiophene-2-boronic acid

Dissolve 2-(5-bromo-4-methyl-thiophen-2-yl)-6-methyl-pyridine (37.6 g, 0.14 mol) and triisopropyl borate (34.2 g, 0.182 mol, 42.3 mL) in toluene (100 mL) and THF (160 mL) under a nitrogen atmosphere. Cool the solution to −40° C. Slowly add n-butyl lithium (2.5 M in hexane, 70 mL, 0.175 mol) using an addition funnel over 40 min. The temperature inside the solution changed from −40° C. to −35° C. Upon complete addition stir the mixture at −40° C. for 2 h. Warm the reaction to 0° C., and add THF (40 mL) and then 2 N aqueous HCl (120 mL) to form a white solid. Add 1 N NaOH until pH=7 and all the salts are dissolved. Separate the organic layer and extract the aqueous layer with diethyl ether (3×). Combine the organic layers, dry over MgSO$_4$, filter, and concentrate. Add THF to the residue and then hexane. Filter the resulting yellow precipitate and repeat the precipitation step several times to afford the title compound (19.7 g, 60%).

$^1$H NMR (CD$_3$OD): δ 2.47 (bs, 3H), 2.61 (s, 3H), 7.20 (d, J=7.7 Hz, 1H), 7.60 (bs, 1H), 7.64 (bd, J=7.7 Hz, 1H), 7.75 (t, J=7.7 Hz, 1H).

Example 15

7-(1-Ethyl-propyl)-2,5-dimethyl-3-[3-methyl-5-(6-methyl-pyridin-2-yl)thiophen-2-yl]-pyrazolo[1,5-a]pyrimidine

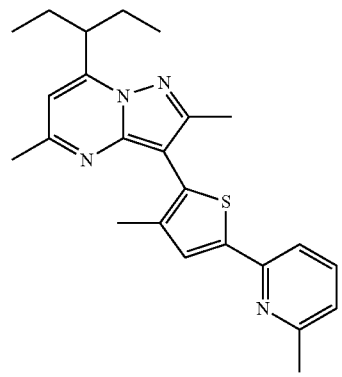

Charge an oven dried flask with 2-(5-boronic acid-4-methyl-thiophen-2-yl)-6-methyl-pyridine (0.29 g, 1.24 mmol), anhydrous toluene (4 mL), absolute ethanol (1 mL), 2 M sodium carbonate (1.1 mL, 2.2 mmol) and 7-(1-ethyl-propyl)-3-iodo-2,5-dimethyl-pyrazolo[1,5-a]pyrimidine (0.25 g, 0.73 mmol). Degas the mixture for 30 min with positive argon pressure and add bis(tri-t-butylphosphine)palladium (0) (0.10 g, 0.086 mmol). Reflux the reaction overnight in an oil bath (100° C.) under an inert atmosphere. Cool the reaction to room temperature and dilute with ethyl acetate (75 mL) and water (25 mL). Separate and extract the aqueous portion with ethyl acetate (50 mL). Combine the organic phases, dry over anhydrous magnesium sulfate, filter, and concentrate under reduced pressure. Purify the resulting residue using flash chromatography, eluting with 100% hexane/0% (25% ethyl acetate/hexane) to 0% hexane/100% (25% ethyl acetate/hexane) in a step gradient of 10% increments to give an off-white foam (0.215 g, 73%). ES/MS m/z 405.4 (M+1)$^+$.

Preparation 13

7-Bromo-thieno[3,2-b]pyridine

Heat thieno[3,2-b]pyridin-7-ol (5.00 g, 33 mmol) and phosphorus oxybromide (50 g, 174 mmol) together at 110° C. for 3 h. Pour the hot reaction mixture into a mixture of ice and 5 N NaOH and extract with CH$_2$Cl$_2$. Dry the organic portion over Na$_2$SO$_4$ and evaporate. Purify the resulting crude material using a silica gel chromatography column (hexane:EtOAC=3:1) to give the title compound (4.19 g, 59%). ES/MS m/z ($^{81}$Br) 215 (M+).

Preparation 14

Thieno[3,2-b]pyridine

Dissolve 7-bromo-thieno[3,2-b]pyridine (3.69 g, 17 mmol) in dry THF (20 mL) and cool to −78° C. Add n-BuLi (1.6 M in hexane, 21.2 mL, 34 mmol) slowly to the mixture at −78° C. and stir at −78° C. for 20 min. Add MeOH/H$_2$O=1/1 (20 mL) and stir at room temperature for 1 h. Extract the reaction mixture with CH$_2$Cl$_2$. Wash the organic portion with saturated NaCl solution, dry over Na$_2$SO$_4$, and evaporate. Purify the resulting residue using silica gel chromatography, eluting with 100% hexane to hexane:ethyl acetate=10:1 to give the title compound (1.44 g, 62%). ES/MS m/z 136 (M+1)$^+$.

Preparation 15

3-Bromo-thieno[3,2-b]pyridine

Combine thieno[3,2-b]pyridine (3.45 g, 25.6 mmol), sodium bicarbonate (2.15 g, 25.6 mmol), K$_2$HPO$_4$ (6.69 g, 38.4 mmol) and MgSO$_4$ (4.01 g, 33.3 mmol) in CHCl$_3$ (60 mL). Stir the mixture under reflux and add Br$_2$ (1.57 mL, 30.7 mmol) slowly. Stir the reaction mixture under reflux overnight. Add more bromine (0.7 mL) and stir the reaction under reflux for 4 h. Cool to room temperature, add water, and extract with CHCl$_3$. Wash the organic portion with saturated Na$_2$S$_2$O$_3$ solution and saturated brine. Dry over Na$_2$SO$_4$ and evaporate. Recrystallize the material from hexane/CH$_2$Cl$_2$ to obtain the title compound (3.94 g, 72%). ES/MS m/z ($^{81}$Br) 215 (M$^+$).

Preparation 16

3-Methyl-thieno[3,2-b]pyridine

Prepare three microwavable reaction vials containing 3-bromo-thieno[3,2-b]pyridine (214 mg, 1.0 mmol) and methylboronic acid (180 mg, 3.0 mmol) in DME/water/EtOH=7/3/1 (4 mL). Add 2 M Na$_2$CO$_3$ (1.5 mL, 3.0 mmol) and bubble in nitrogen gas for 15 min. Add Pd(PPh$_3$)$_4$ (58 mg, 0.05 mmol) and seal the vials. Heat the vials at 130° C. for 30 min in the microwave. Combine all the reaction mixtures, add water and CH$_2$Cl$_2$ and extract. Separate the CH$_2$Cl$_2$ layer, dry over Na$_2$SO$_4$, filter, and evaporate. Purify the resulting material using silica gel chromatography, eluting with hexane:ethyl acetate: 2 M NH$_3$ in MeOH=20:4:1, to give the title compound (193 mg, 43%. ES/MS m/z 150 (M+1)$^+$.

Example 16

7-(1-Ethyl-propyl)-2,5-dimethyl-3-(3-methyl-thieno[3,2-b]pyridin-2-yl)-pyrazolo[1,5-a]pyrimidine

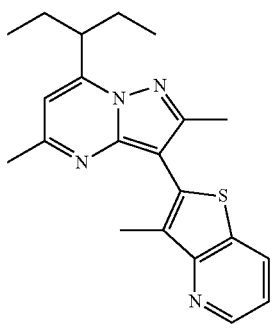

Charge an oven dried schrenk flask with 3-methylthieno[3,2-b]pyridine (0.213 g, 1.42 mmol) and anhydrous THF (5 mL) and cool to −78° C. under an inert atmosphere. Add n-butyl lithium (2.5 M hexane, 0.72 mL, 1.78 mmol) and stir at reduced temperature for 30 min. Add anhydrous zinc chloride (0.58 g, 4.26 mmol) in one aliquot and stir 15 min at reduced temperature. Allow the reaction to warm to room temperature and stir an additional 30 min. Dilute the reaction with anhydrous THF (5 mL) and add 7-(1-ethyl-propyl)-3-iodo-2,5-dimethyl-pyrazolo[1,5-a]pyrimidine (0.406 g, 0.08 mmol). Degas 15 min with positive argon pressure and add dichloro[1,1'-bis(diphenylphosphino) ferrocene]palladium (II) dichloromethane (0.093 g, 0.114 mmol). Reflux the reaction overnight in an oil bath (90° C.) under an inert atmosphere. Cool the reaction to room temperature, quench with saturated ammonium chloride, and dilute with ethyl acetate (75 mL). Separate and extract the aqueous portion with ethyl acetate (50 mL). Combine the organic phases, dry over anhydrous magnesium sulfate, filter, and concentrate under reduced pressure. Purify using flash chromatography, eluting with 100% hexane/0% (15% ethyl acetate/hexane) to 0% hexane/100% (15% ethyl acetate/hexane) in a step gradient of 10% increments to give a white foam (0.059 g, 14%). ES/MS m/z 365.0 (M+1)$^+$.

Example 17

3-[3-Methyl-5-(2-methyl-2H-[1,2,4]triazole-3-yl)-thiophene-2-yl]-7-(1-ethyl-propyl)-2,5-dimethyl-1pyrazolo[1,5-a]pyrimidine Charge an oven dried flask with 1-methyl-1,2,4-triazole (0.320, 3.81 mmol), anhydrous THF (10 mL) and chill to −78° C. under an inert atmosphere. Add n-butyl lithium (2.5 M hexane, 1.52 mL, 3.81 mmol) and stir at reduced temperature for 30 min. Add anhydrous zinc chloride (1.06 g, 7.75 mmol) in one aliquot and stir 15 min at reduced temperature. Allow the reaction to warm to room temperature and stir an additional 30 min. Add 3-(5-bromo-3-methyl-thiophene-2-yl)-7-(1-ethyl-propyl)-2,5-dimethyl-pyrazolo[1,5-a]pyrimidine (0.50 g, 1.27 mmol) in anhydrous THF (5 mL) to the reaction. Degas for 15 min with positive argon pressure and add dichloro[1,1'-bis(diphenylphosphino) ferrocene]palladium (II) dichloromethane (0.147 g, 0.127 mmol). Reflux the reaction overnight in an oil bath (90° C.) under an inert atmosphere. Cool the reaction to room temperature, quench with saturated ammonium chloride, and dilute with ethyl acetate (75 mL). Separate and extract the aqueous portion with ethyl acetate (50 mL). Combine the organic phases, dry over anhydrous magnesium sulfate, filter, and concentrate under reduced pressure. Purify using flash chromatography, eluting with 100% hexane/0% (40% THF/hexane) to 0% hexane/100% (40% THF/hexane) in a step gradient of 10% increments. Triturate the resulting material with hexane/ether (3:1) to give a white solid (0.371 g, 74%). ES/MS m/z 395.0 (M+1)$^+$.

Example 18

3-(5-Nitro-3-methyl-thiophene-2-yl)-7-(1-ethyl-propyl)-2,5-dimethylpyrazolo[1,5-a]pyrimidine Dissolve 3-(3-methyl-thiophene-2-yl)-7-(1-ethyl-propyl)-2,5-dimethyl-pyrazolo[1,5-a]pyrimidine (0.419 g, 1.33 mmol) in dichloromethane (2.5 mL), stir under an inert atmosphere, chill in an ice bath to 0° C. and add trifluoroacetic acid (5 mL). Add concentrated (70%) nitric acid (0.132 g, 1.47 mmol) to the reaction dropwise. The solution changes color from yellow to dark green. Stir 1 h under an inert atmosphere while in an ice bath and confirm the reaction is complete using TLC. Dilute the reaction with dichloromethane (80 mL) and quench with saturated sodium bicarbonate. Separate and extract the aqueous basic phase with dichloromethane (50 mL). Combine the organic phases, dry over anhydrous magnesium sulfate, filter, and concentrate under reduced pressure. Purify the resulting residue using flash chromatography, eluting with 100% hexane/0% (30% ethyl acetate/hexane) to 0% hexane/100% (30% ethyl acetate/hexane) in a step gradient of 10% increments to give a yellow solid (0.363 g, 76%). $^1$H NMR (400 MHz, CDCl$_3$): δ 7.81 (s, 1H), 6.51 (s, 1H), 3.62-3.58 (m, 1H), 2.56 (s, 3H), 2.48 (s, 3H), 2.18 (s, 3H), 1.88-1.70 (m, 4H), 0.88 (t, J=7.5 Hz, 6H).

Example 19

N-{5-[7-(1-Ethyl-propyl)-2,5-dimethylpyrazolo[1,5-a]pyrimidin-3-yl]-4-methyl-thiophen-2-yl}acetamide Dissolve 3-(5-nitro-3-methyl-thiophene-2-yl)-7-(1-ethyl-propyl)-2,5-dimethyl-pyrazolo[1,5-a]pyrimidine (0.33 g, 0.92 mmol) in THF (10 mL) with 10% palladium on carbon (0.10 g), degas with vacuum/hydrogen atmosphere flush (3×) and stir under a hydrogen atmosphere (55 psi) at room temperature for 3 h. Confirm the reaction is complete using TLC. Dilute the reaction with THF (50 mL) and filter through diatomaceous earth, followed by concentration to a crude orange oil (0.328 g). Dissolve the oil in dichloromethane (4 mL) and 1.0 M NaOH (1 mL). Add acetyl chloride (0.038 mL, 0.52 mmol) to the reaction and stir in a sealed reaction vessel at room temperature over the weekend. Dilute the reaction with dichloromethane (100 mL) and wash with water. Collect the organic phase, dry over anhydrous magnesium sulfate, filter, and concentrate to a red oil under reduced pressure. Purify the oil using flash chromatography, eluting with 100% hexane/0% (15% ethyl acetate/10% 7 N ammoniated methanol/75% hexane) to 0% hexane/100% (15% ethyl acetate/10% 7 N ammoniated methanol/75% hexane) in a step gradient of 10% increments to give a brown foam (0.048 g, 26%). ES/MS m/z 371.0 (M+1)$^+$.

Example 20

3-[3-Chloro-5-(2-methyl-2H-[1,2,4]triazole-3-yl)-thiophene-2-yl]-7-(1-propyl-butyl)-2,5-dimethyl-pyrazolo[1,5-a]pyrimidine

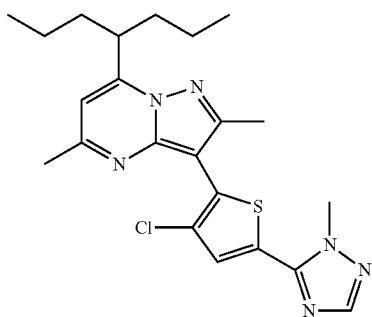

Charge an oven dried flask with 1-methyl-1,2,4-triazole (0.120, 1.43 mmol) and anhydrous THF (5 mL) and chill to −78° C. under an inert atmosphere. Add n-butyl lithium (2.5 M hexane, 0.60 mL, 1.43 mmol) and stir at reduced temperature for 30 min. Add anhydrous zinc chloride (0.400 g, 2.90 mmol) in one aliquot and stir 15 min at reduced temperature. Allow the reaction to warm to room temperature and stir an additional 30 min. Add 3-(5-bromo-3-chloro-thiophene-2-yl)-7-(1-propyl-butyl)-2,5-dimethyl-pyrazolo[1,5a]pyrimidine (0.500 g, 1.27 mmol) in anhydrous THF (5 mL) to the reaction. Degas 15 min with positive argon pressure and add tetrakis(triphenylphosphine) palladium(0) (0.060 g, 0.052 mmol). Reflux overnight in an oil bath (90° C.) under an inert atmosphere. Cool the reaction to room temperature, quench with saturated ammonium chloride, and dilute with ethyl acetate (75 mL). Separate and extract the aqueous portion with ethyl acetate (50 mL). Combine the organic phases, dry over anhydrous magnesium sulfate, filter, and concentrate under reduced pressure. Purify the resulting residue using flash chromatography, eluting with 100% hexane/0% (25% THF/hexane) to 0% hexane/100% (25% THF/hexane) in a step gradient of 20% increments to give a yellow solid (0.140 g, 66%). ES/MS m/z ($^{35}$Cl) 441.7 (M+1)$^+$.

Prepare the following compound essentially as described in Example 20.

| Ex. No. | Chemical name | MS (m/z) |
|---|---|---|
| 21 | 3-[3-Chloro-5-(2-methyl-2H-[1,2,4]triazole-3-yl)-thiophene-2-yl]-7-isopropyl-2,5-dimethyl-pyrazolo[1,5a]pyrimidine | 387.0 (M + 1)$^+$ |

Preparation 17

2-Bromo-5-fluoro-3-methylbenzo[b]thiophene Treat a mechanically stirred solution of 5-fluoro-3-methylbenzo[b]thiophene (50.32 g, 0.303 mol) in acetonitrile (350 mL) with N-bromosuccinimide (56.32 g, 0.318 mol, 1.05 eq). An initial endotherm reduces the reaction temperature to 17° C. A subsequent exotherm then increases the reaction temperature to 40° C. over a 10 min. period, at which time cool the reaction to 18-20° C. by application of an ice water bath. Stir the reaction at room temperature for an additional 35 min and slowly dilute the resultant slurry with water (350 mL). Stir the slurry for 10 min. Filter the product, washing with 50:50 acetonitrile:water (100 mL) and dry to a colorless crystalline solid (65.56 g, 88%).

Example 22

3-(5-Fluoro3-methyl-benzo[b]thiophen-2-yl)-7-isopropyl-2,5-dimethylpyrazolo[1,5-a]pyrimidine

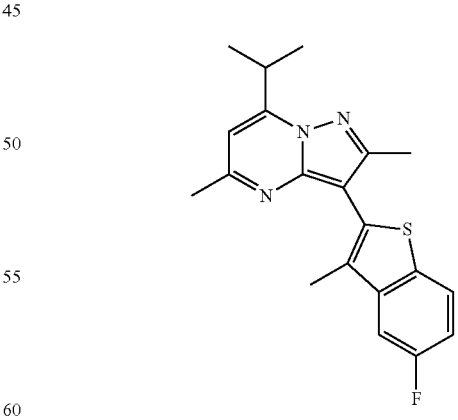

Charge an oven dried flask with 2-bromo-5-fluoro-3-methyl-benzo[b]thiophene (0.490, 2.00 mmol) and anhydrous THF (5 mL) and chill to −50° C. under an inert atmosphere. Add n-butyl lithium (2.5 M hexane, 0.80 mL, 2.0 mmol) dropwise, and stir 30 min. Add anhydrous zinc chloride (0.550 g, 4.00 mmol) in one aliquot and stir 30 min at reduced temperature. Allow the reaction to warm to room temperature and stir an additional 30 min. Add 7-isopropyl-3-iodo-2,5-dimethyl-pyrazolo[1,5a]pyrimidine (0.316 g, 1.00 mmol) in anhydrous THF (5 mL). Degas 15 min with positive argon pressure and add dichloro[1,1'-bis(diphenylphosphino)ferrocene]palladium (II) dichloromethane (0.082 g, 0.1 mmol). Reflux overnight in an oil bath (90° C.) under an inert atmosphere. Cool the reaction to room temperature, quench with saturated ammonium chloride and dilute with ethyl acetate (75 mL). Separate and extract the aqueous portion with ethyl acetate (50 mL). Combine the organic phases, dry over anhydrous magnesium sulfate, filter, and concentrate under reduced pressure. Purify the resulting residue using flash chromatography, eluting with 100% hexane/0% (20% ethyl acetate/hexane) to 0% hexane/100% (20% ethyl acetate/hexane) in a step gradient of 20% increments to yield an off-white foam (0.206 g, 58%). ES/MS m/z 354.0 (M+1)$^+$.

Prepare the following compounds essentially as described in Example 22.

| Ex. No. | Chemical name | MS (m/z) |
|---|---|---|
| 23 | 7-(1-Ethyl-propyl)-3-(5-fluoro-3-methyl-benzo[b]thiophen-2-yl)-2,5-dimethyl-pyrazolo[1,5-a]pyrimidine | (APCI) 382.2 (M + 1)$^+$ |
| 24 | 7-(1-Propyl-butyl)-3-(5-fluoro-3-methyl-benzo[b]thiophen-2-yl)-2,5-dimethyl-pyrazolo[1,5-a]pyrimidine | (APCI) 410.0 (M + 1)$^+$ |

Preparation 18

Boronic acid, 5-fluoro-3-methyl-benzo[b]thiophene-2-yl

In a dry flask combine 5-fluoro-3-methyl-benzo[b]thiophene (312 mg, 1.88 mmol) with dry THF (4 mL). Cool to −78° C. and add n-butyllithium (1.6 N in hexanes, 1.18 mL, 1.90 mmol). Stir 1.5 h at −78° C. and then add trimethylborate (0.23 mL, 2.02 mmol). Stir 3 h and allow the bath to come to −20° C. Add 5 N hydrochloric acid until the reaction is acidic (pH=4). Dilute with water and extract with ethyl acetate (3×). Combine the organic portions, dry over sodium sulfate, filter, and evaporate. Triturate in methylene chloride to obtain a white solid (258 mg, 65%). ES/MS m/z 209 (M−1)$^-$.

Example 25

7-Butyl-3-(5-fluoro-3-methyl-benzo[b]thiophen-2-yl)-2,5-dimethyl-pyrazolo[1,5-a]pyrimidine Add tetrakis(triphenylphosphine)palladium (0) (31 mg, 0.03 mmol) and 7-butyl-3-iodo-2,5-dimethyl-pyrazolo[1,5-a]pyrimidine (174 mg, 0.53 mmol) to degassed anhydrous THF (10 mL). Stir the mixture for 10 min. Add 2-boronic acid-5-fluoro-3-methyl-benzo[b]thiophene (111 mg, 0.53 mmol) and aqueous sodium carbonate solution (112 mg, 1.06 mmol in 5 mL water). Heat the mixture to 70° C. for 24 h. Cool to room temperature. Dilute with ether, then wash with water and brine. Dry the organic phase over magnesium sulfate, filter, and concentrate. Purify the residue by HPLC, eluting with acetonitrile/water/TFA to obtain the title compound (55 mg, 28%). ES/MS m/z 368 (M+1)$^+$.

Preparation 19

4-Chloro-thiophene-2-carbonitrile

Equip a 22-L reaction flask with a cooling bath, air stirrer, gas addition tube, and thermometer probe. Purge the flask with nitrogen, then charge with AlCl$_3$ (1025 g, 7.69 moles) and CHCl$_3$ (6.6 L, 16.5 vol.). Cool the mixture to 0-5° C. and add 2-thiophene carbonitrile (400 g, 3.66 moles) dropwise using an addition funnel over 10-15 min while maintaining the temperature at ≦10° C. Charge the mixture with Cl$_2$ gas (300 g, 4.23 moles, 1.16 eq) subsurface at ≦10° C. over 1.25 h. Monitor the progress of the reaction by GC. Quench an aliquot of the reaction mixture into 6 N HCl, extract with EtOAc, dry over Na$_2$SO$_4$, filter, and inject the filtrate.

When the reaction is complete by GC analysis (consider the reaction to be complete when the ratio of (starting material:product:dichloro material) is approximately (1:5.8:1) by area % GC) add 6 N HCl (8.0 L) dropwise using an addition funnel over 1.5 h, while maintaining the temperature at ≦20° C. The HCl addition is extremely exothermic and evolves gas. Transfer the reaction to a separatory funnel and separate the layers. Extract the aqueous layer with CHCl$_3$ (4.0 L), combine the chloroform layers, and wash with water (6.0 L). Dry the organic portion over Na$_2$SO$_4$, filter, and concentrate under vacuum to give a pale yellow semi-solid (575 g, 109%). GC (60° C. to 280° C. temperature gradient) Area-% analysis shows approx 68% product (t$_{ret}$=6.5 min) with major impurities being the unreacted starting material (t$_{ret}$=5.1 min) and the dichlorinated product (t$_{ret}$=7.4 min). GC Method: Column: DB1; T$_{inject}$=300° C.; T$_{initial}$=60° C., t=2.0 min; T$_{final}$=280° C., rate=18° C./min.

Preparation 20

4-Chloro-2-thiophene carboxamide

Equip a 12-L reaction flask with a cooling bath, air stirrer, and thermometer probe and charge with KOH (288.6 g, 5.143 moles) and water (6.04 L) to form a solution that exotherms to about 31° C. Allow the solution to cool to about 28° C., and charge the mixture with 4-chloro-2-thiophene carbonitrile (671.3 g, 4.675 moles) (a small amount of solids are undissolved). Add EtOH (675 mL), at which time a gradual exotherm occurs and continues over 1-1.5 h to about 38° C. Stir the reaction at ambient temperature overnight. Filter the reaction mixture under vacuum, wash with water, and dry to give crude product. Dissolve the solids in EtOAc (10.0 L), treat with Na$_2$SO$_4$ and activated charcoal for 1-2 h, then filter and wash with EtOAc. Concentrate the filtrate on a rotary evaporator at 45° C. until solids begin to precipitate out. Release the vacuum and increase the temperature to 60-65° C. to redissolve the solids. With stirring at 60° C., add heptane (3.5 L) slowly to precipitate solids. Stir for 15-20 min at 60° C., then cool the mixture to 30-40° C. and filter. Wash the solids with heptane (2×0.75 L), and dry to give the title compound as a white solid (235.4 g, 31%). Obtain a second crop (67.8 g, 9%) from the filtrate.

Preparation 21

4-Chloro-N-dimethylaminomethylene-2-thiophene carboxamide

Equip a 5-L reaction flask with a heating mantle, air stirrer, Dean-Stark apparatus, and thermometer probe. Charge with 4-chloro-2-thiophene carboxamide. (300 g, 1.856 moles) and dimethylformamide dimethylacetal (872 mL) to form a slurry. Heat the mixture gradually to 96° C. while collecting the distillate (mostly MeOH). Remove the heating mantle and cool to ≦25° C. Add water (3.0 L) using an addition funnel and maintain the temperature at ≦35° C. Extract the reaction mixture with EtOAc (3.0 L, 1.5 L). Combine the organics and wash with water (1.5 L). Dry the organic phase over $Na_2SO_4$, filter, and concentrate under vacuum to give the crude product (400 g).

Dissolve the material in EtOAc (320 mL, 0.8 vol) at 50-60° C. Slowly add heptane (1700 mL, 4.25 vol) while gradually increasing the temperature to 70° C. Add a seed crystal to the cloudy solution to initiate precipitation. Stir the resulting mixture at room temperature overnight, then filter and wash with heptane. Dry the solids to give the title compound as a white solid (329.8 g, 82%).

Preparation 22

5-(4-Chloro-thiophen-2-yl)-1-methyl-$^1$H-[1,2,4]triazole

Equip a 3-L reaction flask with a cooling bath, air stirrer, and thermometer probe and charge with 4-chloro-N-dimethylaminomethylene-2-thiophene carboxamide. (155 g, 0.715 moles) and HOAc (1500 mL) to form a solution. Using an ice-water cooling bath to maintain the temperature at ≦30° C., add methylhydrazine (33.2 g, 0.721 moles) dropwise using an addition funnel over 15-20 min to form a light yellow slurry. Heat the reaction gradually to 90° C. and hold at 90° C. for 30 min. Analyze the mixture by GC, then cool the reaction to about 70° C., and concentrate to a thick oil/slurry. Add water (1.67 L) slowly to precipitate solids, cool the mixture to <30° C., filter, and wash with water (1.67 L). Dissolve the wet solids (125.8 g) in warm t-butyl methyl ether (1.64 L), dry over $Na_2SO_4$, filter, and concentrate to dryness to provide the title compound as a pale yellow solid (85.8 g, 60%).

Preparation 23

5-(5-Bromo-4-chloro-thiophen-2-yl)-1-methyl-1H-[1,2,4]triazole

Equip a 3-L reaction flask with a cooling bath, air stirrer, and thermometer probe and charge with 5-(4-Chloro-thiophen-2-yl)-1-methyl-1H-[1,2,4]triazole (105.3 g, 0.527 moles), acetonitrile (1053 mL) and HOAc (105 mL) to form a solution. Add N-bromosuccinimie (103.2 g, 0.580 moles) portion-wise over 30-60 min while maintaining the temperature at ≦31° C. Stir for 1 hour, at which time GC analysis indicates reaction completion. Pour the reaction mixture into water (2.1 L, 20 vol), stir for 30 min, filter, and wash with water (2×1 L). Dry the material in a vacuum oven at 45° C. overnight to give the title compound as a pale yellow solid (123.0 g, 84%).

Example 26

7-Butyl-3-[3-chloro-5-(2-methyl-2H-[1,2,4]triazol-3-yl)-thiophen-2-yl]-2,5-dimethyl-pyrazolo[1,5-a]pyrimidine

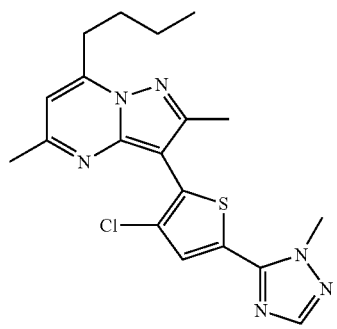

Add 5-(5-bromo-4-chloro-thiophen-2-yl)-1-methyl-1H-[1,2,4]triazole (169 mg, 0.61 mmol) to anhydrous THF (5 mL). Cool to −78° C. Add tert-butyl lithium (0.81 mL, 1.37 mmol, 1.7 M in pentane). Stir for 45 min and then add zinc chloride (1.5 mL, 1.76 mmol, 0.5 M in THF) slowly. Stir for 5 min, then warm to room temperature and stir for 15 min. Add bis(tri-t-butylphosphine)palladium (0) (62 mg, 0.12 mmol) and 7-butyl-3-iodo-2,5-dimethyl-pyrazolo[1,5-a]pyrimidine (200 mg, 0.61 mmol). Heat to reflux overnight. Filter the reaction through Celite® and concentrate to dryness. Purify using silica gel column chromatography, eluting with 0-50% ethyl acetate in hexane, to give the title compound (36 mg, 15%). ES/MS m/z ($^{35}$Cl) 401 (M+1)$^+$.

Example 27

{5-[7-(1-Ethyl-propyl)-2,5-dimethyl-pyrazolo[1,5-a]pyrimidin-3-yl]-4-methyl-thiophen-2-yl}-dimethyl-amine hydrochloride Dissolve 3-(5-nitro-3-methyl-thiophene-2-yl)-7-(1-ethyl-propyl)-2,5-dimethyl-pyrazolo[1,5a]pyrimidine (0.36 g, 1.0 mmol) in THF (5 mL) with 10% palladium on carbon (0.20 g), degas with vacuum/hydrogen atmosphere flush (3×) and stir under a hydrogen atmosphere (55 psi) at room temperature for 3 h. Confirm the reaction is complete using TLC. Dilute the reaction with THF (50 mL) and filter over Celite®. Add sodium hydride as a 60% oil dispersion (0.10 g, 2.25 mmol) and stir 20 min at room temperature. Add iodomethane (0.140 mL, 2.25 mmol) to the reaction and stir in a sealed reaction vessel overnight at 50° C. Quench the reaction with water and dilute with ethyl acetate (100 mL). Wash the organic portion with water, saturated ammonium chloride, and brine. Dry over anhydrous magnesium sulfate, filter, and concentrate to an oil under reduced pressure. Purify the resulting residue using flash chromatography, eluting with 100% hexane/0% (25% ethyl acetate/hexane) to 0% hexane/100% (25% ethyl acetate/hexane) in a step gradient of 10% increments to give a foam (0.145 g, 41%). Dissolve the material (0.13 g, 0.365 mmol) in methanol (3 mL) and add 4.0 M HCl-dioxane (3 mL). Stir the reaction 30 min and blow the reaction down with positive nitrogen pressure. Dry in a vacuum oven to provide a white solid (0.125 g). ES/MS m/z 357.2 (M+1)$^+$.

Example A

In Vivo Potency Assessment Using Ex Vivo Binding

To assess in vivo potency, a compound of the present invention is evaluated using ex vivo binding. Using the procedures as provided in D. R. Gehlert et al., EJP 509: 145-153 (2005), a compound is administered to a rat via the oral route. The binding of $^{125}$I-sauvagine to the cerebellum is then assessed ex vivo as described in Gehlert et al. For example, Example 20 provides 74% inhibition at 10 mg/kg.

Example B

CRF1 Filter Binding Assay

The limitations of plasmid-based human CRF1 expression, in terms of generating a recombinant cell line with sufficient receptor density to develop a binding assay, are overcome by using a Phoenix retroviral expression system licensed from Stanford. The stable HEK-hCRF1 cell line is used to prepare membranes and binding reactions (200 μl) are set up as follows: 50 μl of $^{125}$I-sauvagine (0.2 nM final), 50 μl compound and 100 μl CRF1 membrane (25 μg/reaction). The reactions are incubated at room temperature for 2 hours and then terminated by filtration through pre-treated FB Millipore glass fiber filter plates (96 well). The plates are wash twice with ice-cold assay buffer (50 mM tris, 12.5 mM NaCl, 1 mM EDTA, 10 mM $MgCl_2$, 0.05% BSA, pH 7.2), air dried over night and counted with 100 μl Microscint 40 in a MicroBeta counter. Non-specific binding (NSB) is determined in the presence of 0.5 μM non-labeled sauvagine. Triplicate determinations are typically run and the median data points plotted by Graph Pad Prism.

Using this assay, the exemplified compounds of the present invention (except for Examples 2, 3, 6, 7, and 8, which were used as intermediates for other Examples and were not tested.) inhibit the binding of $^{125}$I-Sauvagine (4 nM) in roller/adherent cells with a Ki (inhibition constant)≦500 nM. For example, Example 20 exhibits a Ki of 4.4 nM.

Example C

CRF2 Filter Binding Assay

The limitations of plasmid-based human CRF2 expression, in terms of generating a recombinant cell line with sufficient receptor density to develop a binding assay, are overcome by using a Phoenix retroviral expression system licensed from Stanford. The stable HEK-hCRF2 cell line is used to prepare membranes and binding reactions (200 μl) are set up as follows: 50 ul of $^{125}$I-sauvagine (0.2 nM final concentration), 50 μl compound and 100 μl CRF2 membrane (25 μg/reaction). The reactions are incubated at room temperature for 2 hours and then terminated by filtration through pre-treated FB Millipore glass fiber filter plates (96 well). The plates are washed twice with ice-cold assay buffer (50 mM tris, 12.5 mM NaCl, 1 mM EDTA, 10 mM $MgCl_2$, 0.05% BSA, pH 7.2), air dried over night and counted with 100 μl Microscint 40 in a MicroBeta counter. Non-specific binding (NSB) is determined in the presence of 0.5 μM non-labeled sauvagine. Alternatively, compounds are evaluated using a Scintillation Proximity assay. This assay is set up as follows: 50 ul of $^{125}$I-Sauvagine (0.2 nM final concentration), 50 μl compound or non-labelled sauvagine (NSB) and 100 μl containing 250 μg wheat germ agglutinin (WGA) SPA beads and CRF2 membrane (1.5 μg/reaction). Plates are incubated for 4-5 hours at room temperature and then centrifuged at 200×g for 10 minutes. Bound radioactivity is assessed using a Wallac Trilux scintillation counter. Binding is assessed typically using triplicate determinations and the median data points plotted by Graph Pad Prism. Compounds are initially screened at a fixed concentration and, if sufficient activity is noted, subsequent concentration-response curves are generated.

Compounds of the present invention preferably exhibit a weak affinity for the CRF2 receptor (relative to CRF1). For example, Example 20 exhibits a 39% inhibition at a concentration of 50 μM.

Example D

Bioavailability and Pharmacokinetic Properties

The volume of distribution (Vdist) relates the amount of the drug in the body to the concentration of the drug in the blood or plasma. The volume of distribution refers to the fluid volume that would be required to contain the total amount of the drug in the body at the same concentration as in the blood or plasma: Vdist=amount of drug in the body/concentration of drug in blood or plasma (Goodman and Gillman's). For a 10 mg dose and a plasma concentration of 10 mg/L, the volume of distribution would be 1 liter. The volume of distribution reflects the extent to which the drug is present in the extravascular tissue. A large volume of distribution reflects the tendency of a compound to bind to the tissue components compared with plasma protein binding. In a clinical setting, Vdist can be used to determine a loading dose to achieve a steady state concentration.

To test for volume of distribution, Male Sprague Dawley rats (N=3) are administered a single 1 mg/kg intravenous dose of compound. Multiple plasma samples are collected at time points from 0.08 to 24 hours post-dose. The plasma samples are analyzed by LC/MS/MS to determine the plasma concentrations. Plasma pharmacokinetic calculations are performed to determine the pharmacokinetic parameters including Vdist and plasma clearance (Clp).

Compounds of the present invention preferably have favorable bioavailability profiles relative to other CRF antagonists such as CP154526 (Schulz et al., *Proc. Natl. Acad. Sci. (USA)*, 93:10477 (1996)) and NBI30775 (Chen et al., *Drug Development Research*, 65:216 (2005)).

We claim:

1. A compound of Formula I

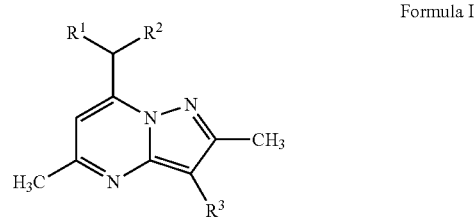

Formula I wherein:
$R^1$ and $R^2$ are independently hydrogen or $C_1$-$C_3$ alkyl;
$R^3$ is

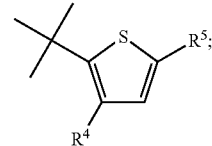

$R^4$ is Cl or methyl;
$R^5$ is

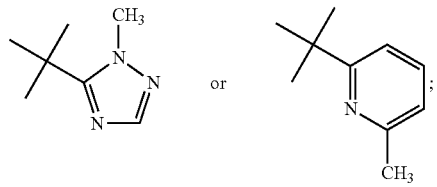

or a pharmaceutically acceptable salts thereof.

2. The compound of claim 1, or a pharmaceutically acceptable salt thereof, wherein $R^1$ and $R^2$ are independently ethyl or n-propyl.

3. A pharmaceutical composition comprising a compound according to claim 1, or a pharmaceutically acceptable salt thereof, and a pharmaceutically acceptable excipient.

4. The compound of claim 1 which is 3-[3-Chloro-5-(2-methyl-2H-[1,2,4]triazole-3-yl)-thiophene-2-yl]-7-(1-propyl-butyl)-2,5-dimethyl-pyrazolo[1,5-a]pyrimidine, or a pharmaceutically acceptable salt thereof.

* * * * *